(12) United States Patent
Mondro et al.

(10) Patent No.: US 8,337,423 B2
(45) Date of Patent: Dec. 25, 2012

(54) BLOOD GLUCOSE SENSOR

(75) Inventors: Jason Mondro, Sparta, NJ (US); David R. Schiff, Highland Park, NJ (US); Jonathan D. Albert, Philadelphia, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 539 days.

(21) Appl. No.: 12/502,594

(22) Filed: Jul. 14, 2009

(65) Prior Publication Data

US 2011/0015546 A1 Jan. 20, 2011

(51) Int. Cl.
*A61B 5/00* (2006.01)
*B65D 81/00* (2006.01)

(52) U.S. Cl. ........................ 600/583; 600/573
(58) Field of Classification Search ................. 600/583, 600/584
See application file for complete search history.

(56) References Cited

U.S. PATENT DOCUMENTS

| | | | |
|---|---|---|---|
| 5,407,554 A | 4/1995 | Saurer | 204/403 |
| 5,437,999 A | 8/1995 | Diebold et al. | |
| 5,741,634 A | 4/1998 | Nozoe et al. | 435/4 |
| 6,143,164 A | 11/2000 | Heller et al. | |
| 6,338,790 B1 * | 1/2002 | Feldman et al. | 205/777.5 |
| 6,558,402 B1 | 5/2003 | Chelak et al. | |
| 6,878,345 B1 | 4/2005 | Astle | |
| 6,881,578 B2 | 4/2005 | Otake | 436/44 |
| 6,893,545 B2 | 5/2005 | Gotoh et al. | 204/403.04 |
| 7,192,405 B2 | 3/2007 | DeNuzzio et al. | 600/583 |
| 7,378,270 B2 | 5/2008 | Azarnia et al. | |
| 7,498,132 B2 | 3/2009 | Yu et al. | 435/6 |
| 7,572,237 B2 * | 8/2009 | Saikley et al. | 600/584 |
| 7,731,900 B2 | 6/2010 | Haar et al. | |
| 2004/0138588 A1 * | 7/2004 | Saikley et al. | 600/583 |
| 2007/0020143 A1 | 1/2007 | Seidenstricker et al. | |
| 2011/0015546 A1 | 1/2011 | Mondro et al. | |
| 2011/0174637 A1 | 7/2011 | Mondro et al. | |

* cited by examiner

*Primary Examiner* — Jeffrey G Hoekstra
(74) *Attorney, Agent, or Firm* — Alan W. Fiedler; Fitzpatrick, Cella, Harper & Scinto

(57) ABSTRACT

The invention is directed to an apparatus and method for blood sample acquisition and testing. The apparatus incorporates a test strip having a blood sample volume detection area in which a blood sample is accumulated and a minimum blood sample volume is detected. Once a minimum blood sample volume is detected, the test strip is moved with respect to the blood sample extraction site so that a bending surface of the test strip is presented to the blood sample, utilizing the surface tension of the blood sample droplet to facilitate movement of the blood sample to a measurement site on the strip where blood glucose in the sample is measured.

12 Claims, 4 Drawing Sheets

BLOOD GLUCOSE SENSOR

BACKGROUND OF THE INVENTION

1. Field of the Invention

The invention is in the field of fluid sample acquisition and testing. In particular, the invention is directed to an apparatus useful for acquisition of a blood sample from a site on a subject's body and testing the blood glucose content of the blood sample utilizing a test strip. The strip may be incorporated into a device adapted for both sampling and sensing in a single step. Methods of using the apparatus are also disclosed.

2. Description of the Related Art

Self monitoring of blood glucose generally requires the user to extract a volume of capillary blood and place it on a disposable element for analysis.

Devices for lancing a subject at an extraction site to obtain a small quantity of blood for testing on a test strip are known in the prior art. For example, U.S. Pat. No. 6,558,402 B1, which is hereby incorporated by reference, discloses a lancer having suitable mechanisms for piercing a subject's skin and obtaining a sample.

Generally, once an incision is made, the extraction site must be "milked" to express fluid from the site, and the fluid must then be transferred to a strip. The trend in test strip devices is toward using ever smaller sample volumes to obtain a measurement. However, even as the sample volume required to obtain a measurement has fallen to the sub-microliter range, it is still generally necessary to express the fluid from the extraction site and transfer the sample to the test strip. Devices and techniques for expressing blood from an incision made by a lancer are disclosed in the prior art, for example in U.S. Pat. Nos. 6,793,633 B2, 6,071,251, and 6,752,817 B2, which are incorporated by reference.

Test strip sensing elements using amperometric and other techniques for determining the concentration of blood glucose in a blood sample are known in the prior art. U.S. Pat. Nos. 6,258,229 B1, 6,143,164 and 5,437,999, incorporated by reference herein, each disclose examples of test strip construction for electrochemical measurement of blood glucose.

An integrated lancet/sensor is disclosed in U.S. Patent Application Publication No. U.S. 2004/0064068, incorporated herein by reference. However, it would be desirable, and would represent an advance over the current state of the art, to provide a more convenient apparatus to obtain a blood sample from an extraction site on a subject, express the blood from the site, and to transport the sample to a measurement site on a test strip without complicated interaction required from the user.

SUMMARY OF THE INVENTION

According to the present invention, a test strip is provided which can be integrated with a lancer so that sample acquisition and testing are facilitated in a single device. The test strip component of the invention is adapted to detect an adequate sample volume for testing, and for relative movement while in a bent state with respect to a blood sample, to facilitate the transport of the blood sample to a measurement site on the test strip.

Specifically, a sensor according to the invention comprises a test strip having conductive contacts positioned thereon defining a blood sample volume detection area. The test strip further has a blood transport channel having a mouth at one end in fluid communication with the blood sample volume detection area and a measurement site at an opposite end of the blood transport channel. The test strip is movable in a bending state between a first position in which the blood sample volume detection area is opposite the blood sample extraction site and a second position in which the mouth of the blood transport channel is opposite the blood sample extraction site. A blood sample bridging the contacts defining the blood sample volume detection area permits electrical communication between the contacts to detect a blood sample volume, and the detected blood sample volume is sufficiently large that the blood sample moves through the blood transport channel to contact the measurement site when the mouth of the blood transport channel is moved to the blood sample extraction site.

A method of using the sensor requires positioning a test strip having a bending portion in a first position over a blood sample extraction site on a subject's body, so that the bending portion of the test strip is opposite the blood sample extraction site. A lancet is passed through the test strip and into a subcutaneous space in the subject's body beneath the sample extraction site and a blood sample is extracted. Blood accumulates in a blood sample volume detection area defined by conductive contacts on the test strip such that contacting the conductive contacts with the blood sample generates a signal when a minimum blood sample volume is detected. As the strip moves, the blood sample is moved through a blood transport channel to a blood glucose measurement site while maintaining the blood transport channel in a bending state and blood glucose in the blood sample is measured at the measurement site.

DETAILED DESCRIPTION OF THE INVENTION

Figure 1:
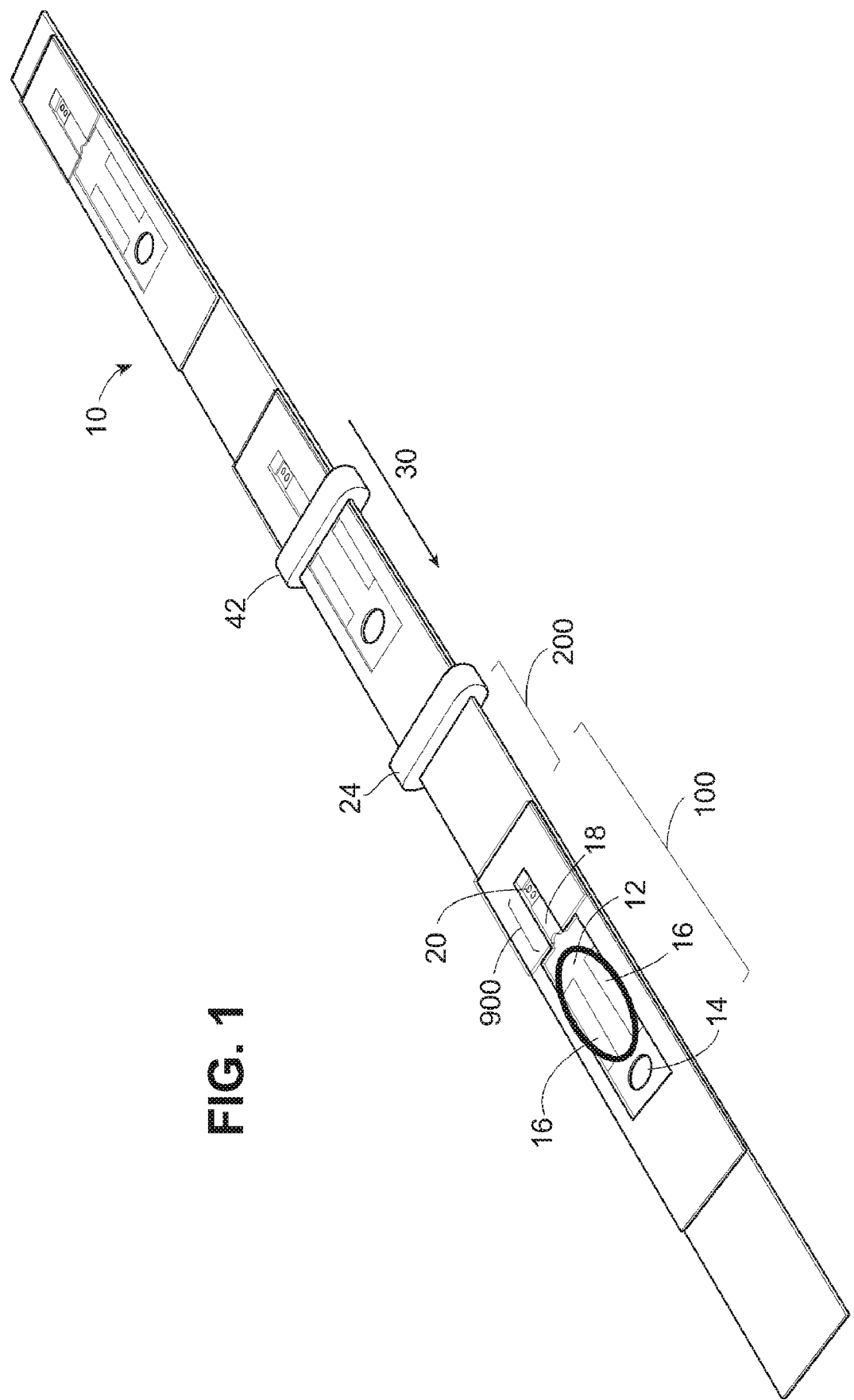
FIG. 1 depicts a continuous test strip according to the invention.

Referring to FIG. 1, test strip 10 generally comprises a blood sample volume detection area 12. In the embodiment shown, a blood sample may be introduced into the volume detection area 12 when piercing hole 14 is pierced by a lancet (not shown in FIG. 1).

The blood sample detection area 12 is defined by contacts 16, such that when a blood sample bridges the contacts, an electrical current flows between the contacts sufficient to indicate that a blood sample of sufficient volume to obtain a measurement has been obtained. The dimensioning and positioning of contacts 16 with respect to the sample detection area 12 is such that only a blood sample of the desired minimum volume will cause electrical current (a volume detection current) to flow between the contacts. The contacts 16 are placed so that they are electrically insulated from one another when a blood sample volume is not present, so the contacts do not short. Further, instrument contacts (not shown) are adapted to receive the signal obtained from the volume detection current for processing. In embodiments, a blood sample sufficient to obtain a measurement is in a range of about 0.2

µL to about 3.0 µL, preferably between about 0.2 µL to about 1 µL, and more preferably in a range of about 0.2 µL to about 0.5 µL.

Blood transport channel 18 has a mouth at one end in fluid communication with the blood sample volume detection area 12. The blood transport channel 18 permits capillary movement of blood sample from the mouth of the channel to measurement site 20. The blood sample detection area 12, the blood transport channel 18 and the measurement site 20 are all located on a functional area 100 of the test strip.

In embodiments, functional areas 100 may be separated by neutral, or non-functional, areas 200, which permits successive functional areas to be located on a single continuous strip. Likewise, seals 24, 42 may be provided between functional areas, or between functional and non-functional areas, to isolate used portions of a strip, or to maintain unused functional areas in a desiccated state within a housing (not shown in FIG. 1). These isolation means (and their equivalents known to those of ordinary skill in the art, or hereafter developed), are useful when a continuous strip is to be used in combination with a housing.

The strip is capable of moving to enable a blood sample to move from the blood sample volume detection area 12 to the blood transport channel 18 and thereafter, by capillary action, to the measurement site 20. In FIG. 1, a direction of movement of the strip is indicated at 30. In the preferred embodiments, the volume of the blood sample detection area 12 and the blood transport 18 channel, taken together, is in a range between about 0.250 µL to about 0.5 µL. The channel may be sized, or tuned, so that the blood sample volume needed to obtain a measurement is just sufficient to allow for the sample to reach the measurement site by capillary motion.

Figure 2A:
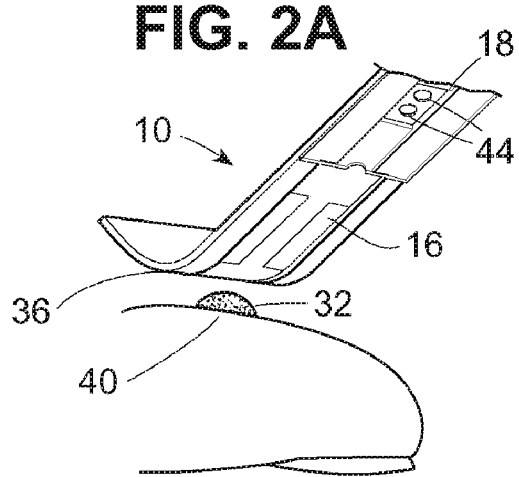
FIG. 2A, FIG. 2B, FIG. 2C, and FIG. 2D each depict the test strip in a bending state at different positions during the use of the test strip to obtain a measurement.

FIG. 2A depicts the test strip 10 in a bending state positioned over a blood sample 32 at an extraction site 40. The inflection 36 of the bend is positioned opposite the extraction site. A "bending state" means that when the strip contacts a sample, the profile of the strip is not a straight line.

Figure 2B:
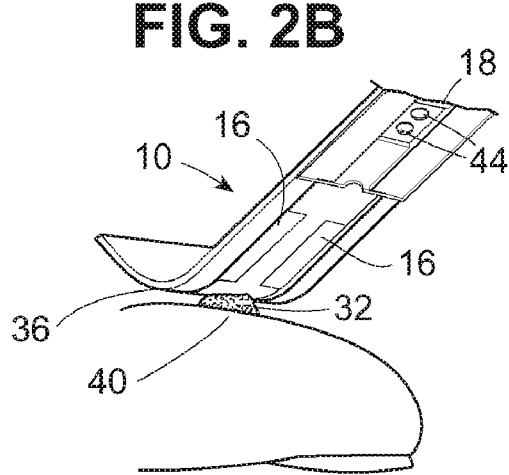

FIG. 2B depicts the test strip 10 with respect to the extraction site 40 in the next position from the position shown in FIG. 2A, after the strip is indexed, or moved. Blood sample 32 is shown accumulated in the blood sample volume detection area 12 defined by conductive contacts 16 on the test strip, such that the blood sample contacts the contacts. Electrical current flowing between the contacts 16 generates a signal, causing indexing of the strip to the next position. Maintaining the test strip in a bent state as the strip contacts the blood sample is believed to maintain the integrity of the blood droplet for a longer period of time, so that the surface tension of the blood sample droplet facilitates the movement of the blood sample toward the blood transport channel 18 with a smaller volume of blood sample than would otherwise be necessary. In effect, the surface tension of the droplet in combination with the movement of the test strip pulls the blood sample in a direction from the blood sample detection area 12 toward the mouth of the blood transport channel 18.

Figure 2C:
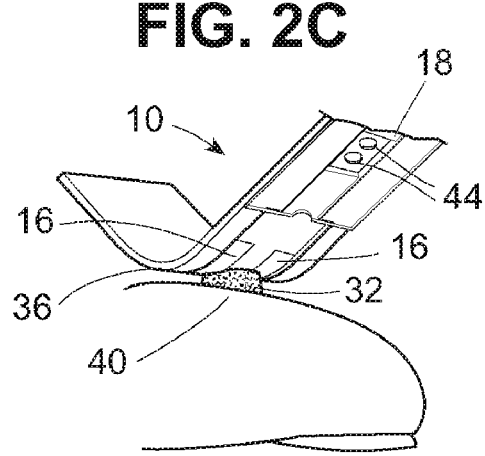

FIG. 2C depicts the test strip 10 with respect to the extraction site 40 in the next position from the position shown in FIG. 2B, after the strip is indexed, in response to the blood volume detection step. The inflection 36 in the strip is at the mouth of the blood transport channel 18, which is positioned over the extraction site.

Figure 2D:
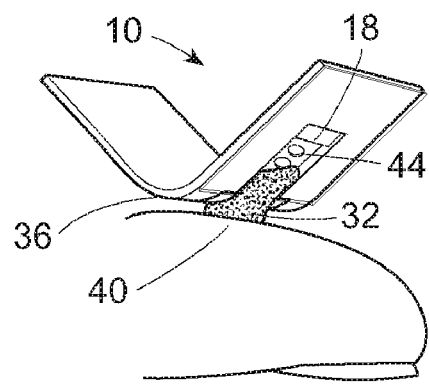

FIG. 2D depicts the inflection 36 in the strip close to the measurement site at a still further position of the strip during use. The blood sample moves by capillary action through the blood transport channel to the reagent wells 44 at the measurement site.

Figure 3:
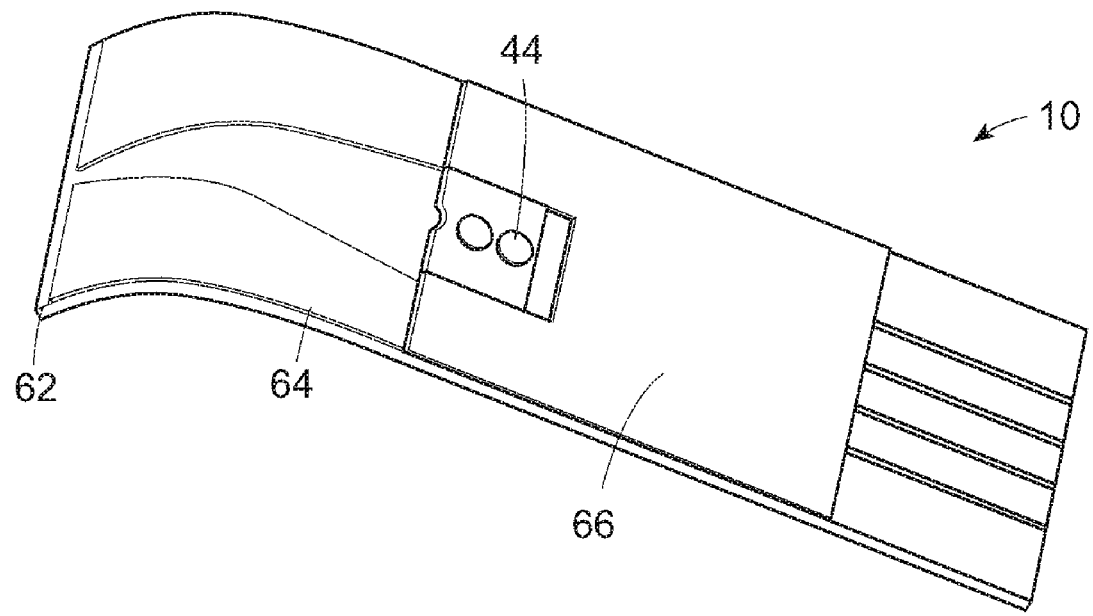
FIG. 3 depicts a discrete test strip according to the invention.

To facilitate the movement of the blood sample 32 by capillary action in the blood transport channel 18, the strip 10 should be constructed of appropriate materials and size. Conveniently for this purpose, the test strip depicted in FIG. 3 (which in this case is a discrete strip) comprises a flexible plastic substrate layer 62 bearing an electrode layer 64 thereon defining separate electrodes: for example, a working electrode, reference electrode and/or counter electrode located in reagent wells 44 at the measurement site. Contacts 16 defining the blood volume detection area, as required, may likewise be defined in the conductive electrode layer. These electrodes must make electrical contact with elements external to the strip so that the strip can be indexed in response to a volume detection signal, and so that the measurement can be obtained, displayed or recorded as desired. A channel forming layer 66, defines a blood transport channel. Surface 12 is advantageously a hydrophobic plastic material.

As shown in FIGS. 2B, 2C and 2D, reagent wells 44 are positioned over electrodes on the test strip. Many configurations of working electrodes, reference electrodes and counter electrodes are known to effect electrochemical measurement of blood glucose content by passing a current between such electrodes in contact with a blood sample. Other methods of measurement are known, including optical methods, wherein a sample induces a color change in a substrate, and the color change is then evaluated by appropriate instrumentation to obtain a value relating to blood glucose content. The structure of the test strip described herein relates to acquisition of a blood sample and the transport of the blood sample to the measurement site 20, and is independent of the method of obtaining a measurement from the strip.

However, as explanation and not by way of limitation, a suitable electrochemical cell for measurement of blood glucose may be made using two relatively inert electrodes formed in areas 44 at the measurement site 20. In a sufficiently sensitive test strip device, the wells defining a working area of the electrodes may have an area of about 0.19 mm$^2$ to about 1.8 mm$^2$. On at least the working electrode, a glucose-responsive reagent is deposited: generally including glucose oxidase enzyme, a redox mediator, and components to permit the reagent to be effectively coated on the electrodes, such as a surfactant and binder. Various reagent chemistries are known in the art and will not be elaborated upon herein When at least the working electrode and counter electrode are in contact with the sample, a reaction at the working electrode occurs involving the blood glucose analyte in the sample. A variable related to the reaction at the working electrode, and the relative potential of the counter or reference electrode with respect to the working electrode may be measured, and the resulting signal may be processed to obtain the glucose concentration. Various algorithms are known to obtain these values, and to correct the values obtained for environmental factors. It is not critical, for example, that current is the measured variable, how that signal is processed or what method of measurement is used in the apparatus, and any such method known in the art or hereafter developed may be employed.

An important aspect of the invention is that the test strip is held in a bent state as it contacts the blood sample, and the inflection 36 of the bend moves along the strip during use, causing the blood sample to move with it. To achieve this, several configurations are possible.

Figure 4:
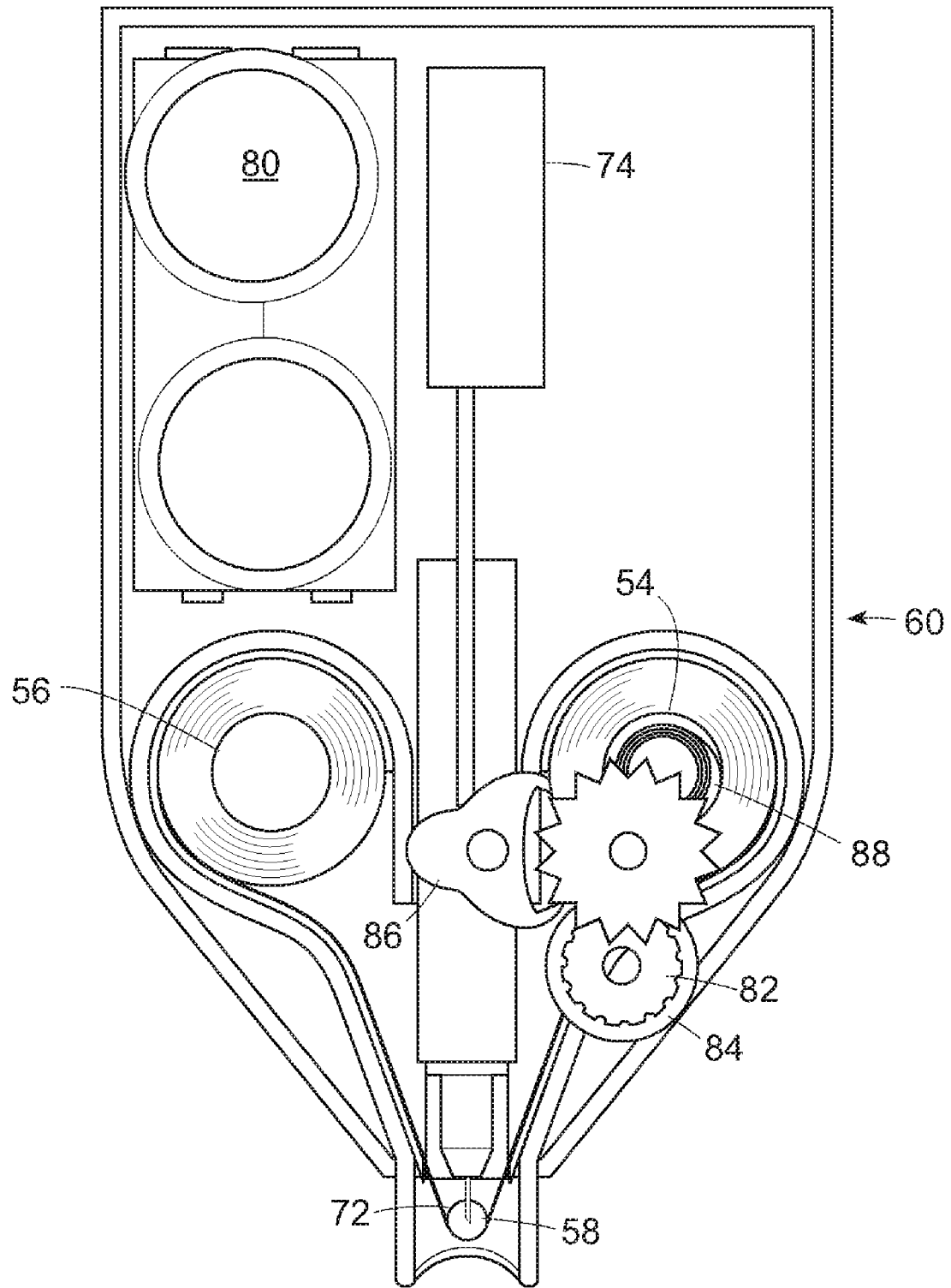
FIG. 4 depicts an alternative embodiment in which a lancet and a continuous test strip are contained within a housing.

FIG. 4 depicts a configuration in which the test strip is continuous (as in FIG. 1), such that multiple functional areas may be wound on storage roller 56 and contained within a housing 60. Bending roller 58 provides a bending support supporting the strip in the bending state opposite the blood sample extraction site and used portions of the strip are taken up by take-up roller 54. Lancet 72 is connected to a lancet plunger system 74. While not limiting, a suitable plunger and lancet design for use in connection with this invention is disclosed in the aforesaid U.S. Pat. No. 6,558,402 B1. The lancet is arranged in housing 60 so that upon suitable triggering, the lancet is plunged through the piercing hole 14 within or near the blood volume detection area 12 and into a subcutaneous space underneath the subject's skin. Given the particular embodiment shown in FIG. 1, the glucose sensor element is maintained in a desiccated state within the housing behind one seal 42 while the used sensors are maintained behind second seal 24. The seals are advantageously made of an elastomeric material to ensure a snug fit in the opening of the housing where they are positioned, such that the seals can be pulled through the openings when the strip is indexed from one position to the next. Appropriate power elements 80 and an associated metering device (not shown) may also be provided within housing 60.

Roller 54 may serve as means for advancing the functional areas 100 on the test strip. As shown in FIG. 4, roller 54 bearing the test strips is mounted with negator spring 88 preventing free movement of the continuous strip. Sprocket drive 84 engages the strip and functions with gear 82 and with escapement mechanism 86 to index the test strip by a predetermined amount on roller 54 when the device is fired, in response to signals that a blood sample volume has been detected, or in response to a signal generated when a measurement has been completed.

The drive mechanism is preferably in operative communication with a device for receiving the signal relating to the blood volume detection step and with a device for measuring, displaying and/or recording blood glucose measurements so that every aspect of the acquisition and sensing is integrated. For this purpose a suitable microprocessor may be used.

When a lancer and a strip are combined in a single device, or within a housing, as described above, the strip should be positioned with respect to the lancer so that the lancer is capable of piercing the test strip at a specified location, such as piercing hole 14, so that blood is accumulated in the blood sample detection area. It may be desirable to incorporate means for expressing fluid from the blood sample extraction site onto the strip.

Figure 5:
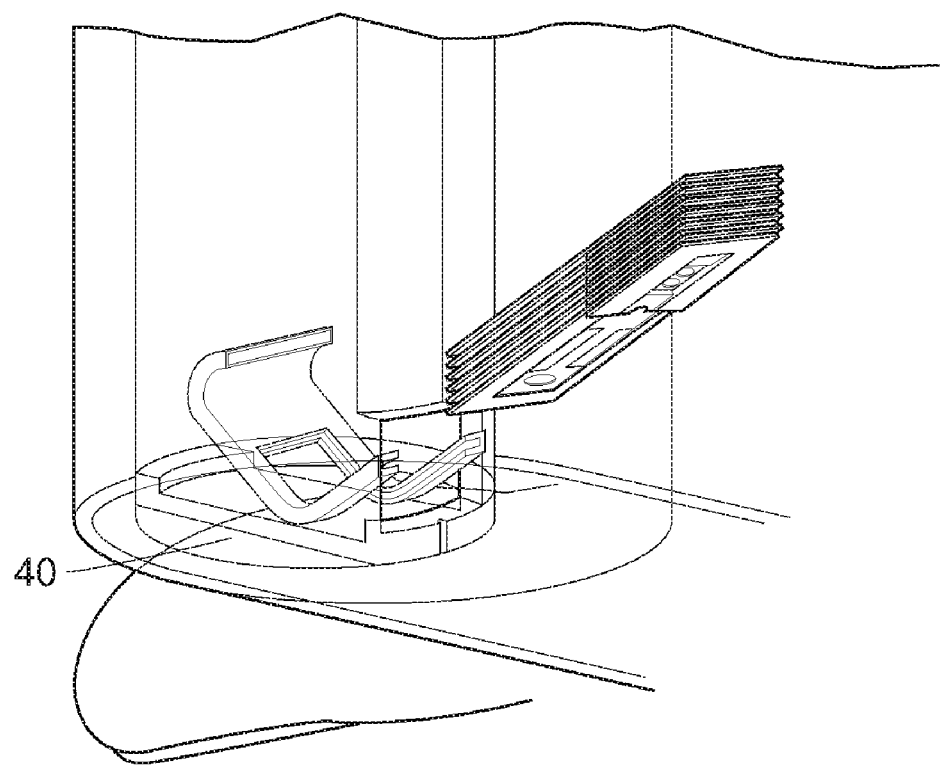
FIG. 5 depicts a cartridge for holding a plurality of discrete test strips.

Other bending surfaces may be used to support the bending portion of the test strip in the bending state. FIG. 5 discloses a cartridge system for containing a plurality of test strips. The cartridge feeds individual test strips past a guide member which serves as the bending surface presenting the test strip in a bending state to the blood sample extraction site 40 on the subject. Thus, the strips need not be contained within a housing together with the lancet in order to be moved in a bending state. All that is required is means to sense a current from contacts 16 when a minimum volume blood sample is obtained on the strip. Therefore, contacts 16 must be in electrical communication with an element external to the strip at some point during use. One of ordinary skill in the art of test strip design may configure a plurality of test strips or functional areas in a circular configuration on a disc or drum for serial use, provided the strip is capable of presenting a bent portion to the blood sample extraction area.

The foregoing description of the explanatory embodiments is not to be considered as limiting the subject invention, which is defined by the claims appended hereto.

What is claimed is:

1. A blood glucose sensor for measuring blood glucose in a blood sample withdrawn from a blood sample extraction site on a subject's body, comprising:
   a test strip;
   conductive contacts positioned on the test strip and defining a blood sample volume detection area;
   said test strip having a blood transport channel having a mouth at one end in fluid communication with the blood sample volume detection area; and
   a measurement site at an opposite end of the blood transport channel;
   the test strip being bent at a plurality of inflections and moved between a first inflection at which the blood sample volume detection area is opposite the blood sample extraction site and a second inflection at which the mouth of the blood transport channel is opposite the blood sample extraction site,
   wherein a blood sample bridging the contacts defining the blood sample volume detection area permits electrical communication between the contacts to detect a blood sample volume; and
   wherein the detected blood sample volume is sufficiently large that the blood sample moves through the blood transport channel to contact the measurement site when the mouth of the blood transport channel is moved to said blood sample extraction site.

2. The blood glucose sensor of claim 1, further comprising a bending surface supporting the test strip when bent at an inflection opposite the blood sample extraction site.

3. The blood glucose sensor of claim 2, wherein the bending surface is a roller and the test strip is movable over the roller between the first and second inflections.

4. The blood glucose sensor of claim 3, wherein the test strip arranged on the roller is continuous, having a plurality of functional areas, each functional area on the test strip comprising a volume detection area, blood transport channel and measurement site, and each functional area is separated by a neutral portion, the functional areas being arranged on the test strip for successive blood glucose measurements.

5. The blood glucose sensor of claim 4, further comprising a housing and a lancet arranged in the housing to pass through the test strip at the blood volume detection area and to withdraw a blood sample from a subcutaneous space in a subject's body beneath the blood sample extraction site.

6. The blood glucose sensor of claim 5, further comprising a first seal isolating the functional areas of the test strip that have been used for blood glucose measurement from an environment outside of the housing, and a second seal isolating the unused areas of test strip from the environment.

7. The blood glucose sensor of claim 1, further comprising a cartridge containing a plurality of test strips, and a guide member for bending each individual test strip at a plurality of inflections opposite a blood sample extraction site on a patient's body.

8. The blood glucose sensor of claim 1, wherein the blood sample volume detection area is sized so that a blood sample having a volume of about 0.2 µL to about 1.0 µL causes the blood sample to contact the conductive contacts in the blood sample volume detection area to generate a signal indicating that a minimum blood sample volume has been obtained.

9. The blood glucose sensor of claim 1, wherein the bent portion of the test strip contacts a blood sample on the blood sample extraction site so that surface tension of the blood sample in combination with the movement of the test strip pulls the blood sample in a direction from the blood sample volume detection area to the mouth of the blood transport channel.

10. The blood glucose sensor of claim 1, comprising an optical sensor for measuring blood glucose in the blood sample at the measurement site.

11. The blood glucose sensor of claim 1, comprising an electrochemical sensor for measuring blood glucose in the blood sample at the measurement site.

12. The blood glucose sensor of claim 2, comprising a plurality of test strips in a circular configuration on a disc or drum.

* * * * *